(12) United States Patent
Schweizer et al.

(10) Patent No.: US 7,611,735 B2
(45) Date of Patent: Nov. 3, 2009

(54) CANOLA PROTEIN ISOLATE

(75) Inventors: Martin Schweizer, Winnipeg (CA); Brent E. Green, Winnipeg (CA); Kevin I. Segall, Winnipeg (CA); Randy Willardsen, Roseville, CA (US)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 0 days.

(21) Appl. No.: 10/586,264

(22) PCT Filed: Jan. 20, 2005

(86) PCT No.: PCT/CA2005/000062

§ 371 (c)(1),
(2), (4) Date: May 22, 2007

(87) PCT Pub. No.: WO2005/067729

PCT Pub. Date: Jul. 28, 2005

(65) Prior Publication Data

US 2007/0244300 A1    Oct. 18, 2007

Related U.S. Application Data

(60) Provisional application No. 60/537,031, filed on Jan. 20, 2004.

(51) Int. Cl.
*A01N 65/00* (2006.01)
*A61K 36/00* (2006.01)

(52) U.S. Cl. ..................................... 424/725

(58) Field of Classification Search .................. None
See application file for complete search history.

(56) References Cited

U.S. PATENT DOCUMENTS

2003/0224099 A1* 12/2003 Hiron ..................... 426/615
2004/0034200 A1*  2/2004 Logie et al. ............. 530/377

* cited by examiner

*Primary Examiner*—Michele Flood
*Assistant Examiner*—Qiuwen Mi
(74) *Attorney, Agent, or Firm*—Sim & McBurney; Michael I. Stewart

(57) ABSTRACT

A canola protein isolate consisting predominantly of 2S canola protein and having improved solubility properties, has an increased proportion of 2S canola protein and a decreased proportion of 7S canola protein. The canola protein isolate is formed by heat treatment of aqueous supernatant from canola protein micelle formation and precipitation, to effect precipitation of 7S protein which is sedimented and removed. Alternatively, the canola protein isolate may be derived from a selective membrane procedure in which an aqueous canola protein solution containing 12S, 7S and 2S canola proteins is subjected to a first selective membrane technique to retain 12S and 7S canola proteins in a retentate, which is dried to provide a canola protein isolate consisting predominantly of 7S canola protein, and to permit 2S canola protein to pass through the membrane, the permeate is subjected to a second selective membrane technique to retain 2S canola protein and to permit low molecular weight contaminants to pass through the membrane, and the retentate from the latter membrane technique is dried.

7 Claims, 1 Drawing Sheet

CANOLA PROTEIN ISOLATE

FIELD OF INVENTION

The present invention relates to the production of canola protein isolates.

BACKGROUND TO THE INVENTION

Canola oil seed protein isolates having protein contents of at least 100 wt % (N×6.25) can be formed from oil seed meal by a process as described in copending U.S. patent application Ser. No. 10/137,391 filed May 3, 2002 (WO 02/089597), assigned to the assignee hereof and the disclosures of which are incorporated herein by reference. The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process, the supernatant from the PMM settling step is processed to recover canola protein isolate from the supernatant. This procedure may be effected by initially concentrating the supernatant using an ultrafiltration membrane and drying the concentrate. The resulting canola protein isolate has a protein content of at least about 90 wt %, preferably at least about 100 wt % (N×6.25).

The procedures described in U.S. patent application Ser. No. 10/137,391 are essentially batch procedures. In copending U.S. patent application Ser. No. 10/298,678 filed Nov. 19, 2002 (WO 03/043439), assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously conveyed through a selective membrane operation to increase the protein content of the aqueous protein solution to at least about 50 g/L, while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is recovered from the settling vessel and may be dried. The PMM has a protein content of at least about 90 wt % (N×6.25), preferably at least about 100 wt %. The overflowed supernatant may be processed to recover canola protein isolate therefrom, as described above.

Canola seed is known to contain about 10 to about 30 wt % proteins and several different protein components have been identified. These proteins include a 12S globulin, known as cruciferin, a 7S protein and a 2S storage protein, known as napin. As described in copending U.S. patent application Ser. No. 10/413,371 filed Apr. 15, 2003 (WO 03/088760), assigned to the assignee hereof and the disclosures of which are incorporated herein by reference, the procedures described above, involving dilution of concentrated aqueous protein solution to form PMM and processing of supernatant to recover additional protein, lead to the recovery of isolates of different protein profiles.

In this regard, the PMM-derived canola protein isolate has a protein component content of about 60 to about 98 wt % of 7S protein, about 1 to about 15 wt % of 12S protein and 0 to about 25 wt % of 2S protein. The supernatant-derived canola protein isolate has a protein component content of about 60 to about 95 wt % of 2S protein, about 5 to about 40 wt % of 7S protein and 0 to about 5 wt % of 12S protein. Thus, the PMM-derived canola protein isolate is predominantly 7S protein and the supernatant-derived canola protein isolate is predominantly 2S protein. As described in the aforementioned U.S. patent application Ser. No. 10/413,371, the 2S protein has a molecular size of about 14,000 daltons, the 7S protein has a molecular mass of about 145,000 daltons and the 12S protein has a molecular size of about 290,000 daltons.

Canola is also known as rapeseed or oil seed rape.

SUMMARY OF INVENTION

It has now surprisingly been found that a canola protein isolate having an increased proportion of 2S protein, preferably containing at least about 85 wt % of 2S protein, and having a reduced proportion of 7S protein exhibits superior properties in aqueous solution to the supernatant-derived canola protein isolate prepared following the procedure of the aforementioned U.S. patent application Ser. No. 10/137,391.

In addition to improved solubility at a variety of pH values, the canola protein isolate provided herein is able to provide improved clarity in solution with soft drinks, providing clear protein fortified soft drinks.

Accordingly, in one aspect of the present invention, there is provided a canola protein isolate consisting predominantly of 2S canola protein having a protein content of at least about 90 wt % of (N×6.25) on a dry weight basis (d.b.) and having an increased proportion of 2S canola protein and a decreased proportion of 7S canola protein when compared to canola protein isolates consisting predominantly of 2S canola protein and derived from aqueous supernatant from canola protein micelle formation and precipitation.

In a further aspect of the present invention, there is provided a canola protein isolate having a protein content of at least about 90 wt % (N×6.25) on a dry weight basis (d.b.) and containing at least about 85 wt % of 2S canola protein and less than about 15 wt % of 7S canola protein of the canola proteins present in the isolate.

The canola protein isolate may be prepared by thermal treatment of the concentrated supernatant from the procedure of U.S. patent application Ser. No. 10/137,391 in order to reduce the proportion of 7S protein in the concentrated supernatant and hence to increase the proportion of 2S protein. Accordingly, in another aspect of the present invention, there is provided a process for the preparation of a canola protein isolate having an increased proportion of 2S canola protein, which comprises (a) providing an aqueous solution of 2S and 7S proteins consisting predominantly of 2S protein, (b) heat treating the aqueous solution to cause precipitation of 7S canola protein, (c) removing degraded 7S protein from the aqueous solution, and (d) recovering a canola protein isolate having a protein content of at least about 90 wt % (N×6.25) d.b. and having an increased proportion of 2S canola protein.

Alternatively, the canola protein isolate may be prepared by a procedure in which, following extraction of protein from the canola oil seed meal, the protein solution is subjected to a first selective membrane step with a membrane having a molecular weight cut-off which permits the 2S protein to pass through the membrane in a permeate while the 7S and 12S proteins are retained in a retentate. The retentate then is dried to provide a first canals protein isolate which is predominantly 7S protein. The permeate from the first selective membrane process step is then subjected to a second selective membrane step with a membrane having a molecular weight cut-off which retains the 2S protein and permits low molecular weight contaminants, including salt, phenolics and anti-nutritional materials, to pass through. The retentate from the latter selective membrane step then is dried to provide a second canola protein isolate which is predominantly 2S protein and which is the protein isolate.

Accordingly, in an additional aspect of the present invention, there is provided a process for the preparation of a canola protein isolate, which comprises (a) providing an aqueous canola protein solution derived from canola oil seed meal and containing 12S, 7S and 2S canola proteins, (b) increasing the protein concentration of the aqueous solution using a selective membrane technique which is effective to retain 7S and 12S canola proteins in a retentate and to permit 2S protein to pass through the membrane as a permeate to provide a concentrated protein solution, (c) drying the retentate from step (b) to provide a canola protein isolate consisting predominantly of 7S canola protein and having a protein content of at least about 90 wt % (N×6.25) on a dry weight basis (d.b.), (d) increasing the concentration of the permeate from step (a) using a selective membrane technique which is effective to retain 2S canola protein in a retentate and to permit low molecular weight contaminants to pass through the membrane in a permeate, and (e) drying the retentate from step (d) to provide a canola protein isolate consisting predominantly of 2S protein and having a protein content of at least about 90 wt % (N×6.25) d.b.

GENERAL DESCRIPTION OF INVENTION

Figure 1:
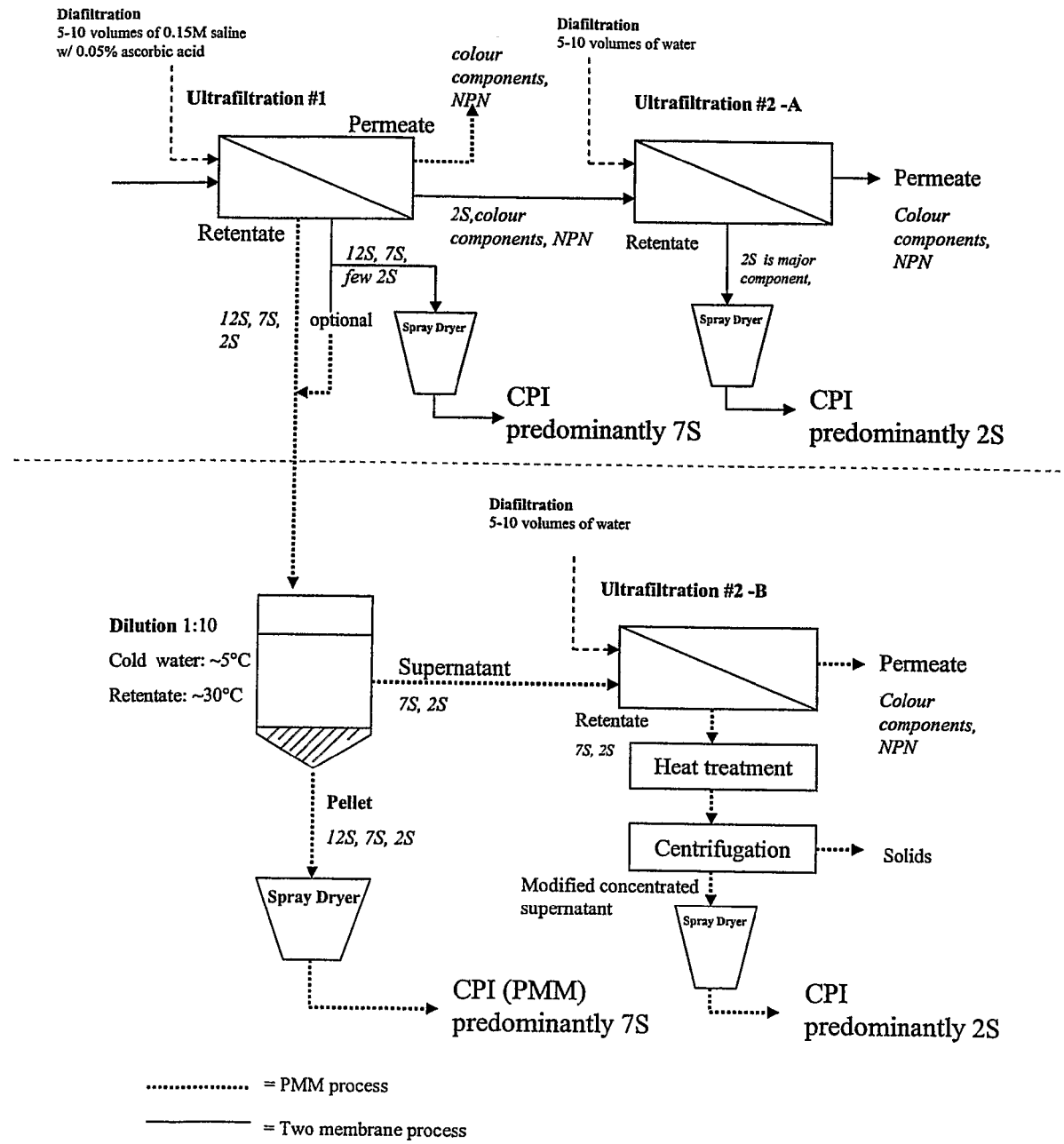
FIG. 1 is a schematic representation of a protein solution recovery process according to one embodiment of the invention superimposed on the protein micelle process.

The canola protein isolate provided herein has a protein content of at least about 90 wt % (N×6.25), preferably at least about 100 wt %, and may be isolated from canola oil seed meal by a batch process, or a continuous process, or a semi-continuous process.

The canola protein isolate provided herein consists predominantly of 2S protein and has an increased proportion of 2S canola protein and a decreased proportion of 7S canola protein when compared to canola protein isolates consisting predominantly of 2S protein and derived from supernatant from canola protein micelle formation and precipitation and prepared under the same experimental conditions of preparation.

The canola protein isolates contain at least about 85 wt % of 2S canola protein and less than about 15 wt % of 7S canola protein, preferably at least about 90 wt % of 2S canola protein and less than about 10 wt % of 7S canola protein and more preferably as great a proportion of 2S protein as is possible. As noted above, such canola protein isolate may be obtained by heat treatment of concentrated supernatant, as described in more detail below. The heat treatment of the concentrated supernatant causes precipitation of the 7S protein, which can be removed from the heat-treated supernatant by any convenient means, such as centrifugation. The 2S protein is not affected by the heat treatment and hence the heat treatment increases the proportion of 2S protein present by decreasing the proportion of 7S protein.

The canola protein isolate is soluble in aqueous solution over a wide range of pH values, generally having greater solubility than canola protein isolate consisting predominantly of 2S protein and derived from supernatant from canola protein micelle formation and precipitation under the same experimental conditions of preparation. In addition, aqueous solutions of the canola protein isolate in soft drinks, including carbonated soft drinks, such as those commercially-available, have a greater clarity than such aqueous solutions produced from canola protein isolate consisting predominantly of 2S protein and derived from supernatant from canola protein micelle formation and precipitation under the same conditions of preparation.

The concentration of canola protein isolate in the aqueous solution, including solution in soft drinks, may vary depending on the intended use of the solution. In general, the protein concentration may vary from about 0.1 to about 30 wt %, preferably about 1 to about 5 wt %.

The initial step of the process of providing canola protein isolates involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 0.8, and more preferably a value of about 0.1 to about 0.15.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effected at elevated temperatures, preferably at least about 35° C., generally up to about 65° C. or more.

The aqueous food grade salt solution generally has a pH of about 5 to about 6.8, preferably about 5.3 to about 6.2, the pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfate or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution discussed below and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operations.

Another alternative procedure is to extract the oil seed meal with the food grade salt solution at a relatively high pH value above about 6.8, generally Lip to about 9.9. The pH of the food grade salt solution, may be adjusted in pH to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing decanter centrifugation, followed by disc centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution may be processed in two alternative procedures, depending on whether 7S-rich protein micellar mass is to be precipitated to leave a supernatant for processing to form the canola protein isolate, or the aqueous protein solution is to be processed by a two-membrane operation without precipitation of protein micellar mass to obtain the canola protein isolate.

In the first alternative procedure, the aqueous protein solution is concentrated to increase the protein concentration thereof while maintaining the ionic strength thereof substantially constant. Such concentration generally is effected to provide a concentrated protein solution having a protein concentration of at least about 50 g/L, preferably at least about 200 g/L, more preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous protein solution by passage through the membrane with the permeate. The diafiltration operation may be effected until no significant further quantities of phenolics and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrating of the protein solution to the preferred concentration above about 200 g/L in this step not only increases the process yield to levels above about 40% in terms of the proportion of extracted protein which is recovered as dried protein isolate, preferably above about 80%, but also decreases the salt concentration of the final protein isolate after drying. The ability to control the salt concentration of the isolate is important in applications of the isolate where variations in salt concentrations affect the functional and sensory properties in a specific food application.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour absorbing agent is polyvinyl pyrrolidone.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour absorbing agent, an amount of about 0.5% to about 5% w/v, preferably about 2% to about 3% w/v, may be used. The colour absorbing agent may be removed from the canola protein solution by any convenient means, such as by filtration.

The concentrated and optionally diafiltered protein solution resulting from the optional colour removal step may be subjected to pasteurization to kill any bacteria which may have been present in the original meal as a result of storage or otherwise and extracted from the meal into the canola protein isolate solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

Depending on the temperature employed in the concentration step and optional diafiltration step and whether or not a pasteurization step is effected, the concentrated protein solution may be warmed to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which micelle formation does not occur on dilution by chilled water.

The concentrated protein solution resulting from the concentration step, and optional diafiltration step, optional colour removal step, optional pasteurization step and optional defatting step, then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With higher dilution levels, in general, a greater proportion of the canola protein remains in the aqueous phase.

When it is desired to provide the greatest proportion of the protein by the micelle route, the concentrated protein solution is diluted by about 15 fold or less, preferably about 10 fold or less.

The chilled water with which the concentrated protein solution is mixed has a temperature of less than about 15° C., generally about 30 to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution of the concentrated protein solution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel. In lieu of settling by sedimentation, the PMM may be separated continuously by centrifugation.

The combination of process parameters of concentrating of the protein solution to a preferred protein content of at least about 200 g/L and the use of a dilution factor less than about 15, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned US patents.

By the utilization of a continuous process for the recovery of canola protein isolate as compared to the batch process, the initial protein extraction step can be significantly reduced in time for the same level of protein extraction and significantly higher temperatures can be employed in the extraction step. In addition, in a continuous operation, there is less chance of contamination than in a batch procedure, leading to higher product quality and the process can be carried out in more compact equipment.

The settled isolate is separated from the residual aqueous phase or supernatant, such as by decantation of the residual aqueous phase from the settled mass or by centrifugation. The PMM may be used in the wet form or may be dried, by any convenient technique, such as spray drying or freeze drying, to a dry form. The dry PMM has a high protein content, in excess of about 90 wt % protein, preferably at least about 100 wt % protein (calculated as Kjeldahl N×6.25), and is substantially undenatured (as determined by differential scanning calorimetry). The dry PMM isolated from fatty oil seed meal also has a low residual fat content, when the procedures of U.S. Pat. Nos. 5,844,086 and 6,005,076 are employed as necessary, which may be below about 1 wt %.

As described in the aforementioned U.S. patent application Ser. No. 10/413,371, the PMM consists predominantly of a 7S canola protein having a protein component content of about 60 to 98 wt % of 7S protein, about 1 to about 15 wt % of 12S protein and 0 to about 25 wt % of 2S protein.

The supernatant from the PMM formation and settling step contains significant amounts of canola protein, not precipitated in the dilution step, and is processed to recover canola protein isolate therefrom. As described in the aforementioned U.S. patent application Ser. No. 10/413,371, the canola protein isolate derived from the supernatant consists predominantly of 2S canola protein having a protein component content of about 60 to about 95 wt % of 2S protein, about 5 to about 40 wt % of a 7S protein and 0 to about 5 wt % of 12S protein.

The supernatant from the dilution step, following removal of the PMM, is concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the supernatant in this way also reduces the volume of liquid required to be dried to recover the protein. The supernatant generally is concentrated to a protein concentration of at least about 50 g/L, preferably about 100 to about 400 g/L, more preferably about 200 to about 300 g/L, prior to drying. Such concentration operation may be carried out in a batch mode or in a continuous operation, as described above for the protein solution concentration step.

The concentrated supernatant then may be subjected to a diafiltration step using water. Such diafiltration may be effected using from about 2 to about 20 volumes of diafiltration solution, preferably about 5 to about 10 volumes of diafiltration solution. In the diafiltration operation, further quantities of contaminants are removed from the aqueous supernatant by passage through the membrane with the permeate. The diafiltration operation may be effected until no significant further quantities of phenolics and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diaflitration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

In accordance with the present invention, the concentrated and optionally diafiltered supernatant is heat treated to decrease the quantity of the 7S protein present in the solution by precipitation and removal of the 7S protein and thereby increasing the proportion of 2S protein in the canola protein present in the concentrated supernatant.

Such heat treatment may be effected using a temperature and time profile sufficient to decrease the proportion of 7S present in the concentrated supernatant, preferably to reduce the proportion of 7S protein by a significant extent. In general, the 7S protein content of the supernatant is reduced by at least about 50 wt %, preferably at least about 75 wt % by the heat treatment. In general, the heat treatment may be effected at a temperature of about 70° to about 100° C., preferably about 75 to about 95° C., for about 2 to about 30 minutes, preferably about 5 to about 15 minutes. The precipitated 7S protein may be removed in any convenient manner, such as centrifugation or filtration.

The concentrated heat-treated supernatant, after removal of the degraded 7S protein, such as by centrifugation, may be dried by any convenient technique, such as spray drying or freeze drying, to a dry form to provide a canola protein isolate in accordance with the present invention. Such canola protein isolate has a high protein content, in excess of about 90 wt %, preferably at least about 100 wt % protein (calculated as Kjeldahl N×6.25) and is substantially undenatured (as determined by differential scanning calorimetry).

Such canola protein isolate contains a high proportion of 2S protein, preferably at least 90 wt % and most preferably at least about 95 wt %, of the canola protein in the isolate.

In an alternative procedure to produce the canola protein isolate, the aqueous protein solution produced by extraction of the canola oil seed protein meal is concentrated to increase the protein concentration thereof while maintaining the ionic strength thereof substantially constant by a first ultrafiltration step using membranes, such as hollow-fibre membranes or spiral wound membranes, having a molecular weight cut-off sufficient to retain the 7S and 12S proteins in a retentate and to permit 2S protein to pass through the membrane. A suitable molecular weight cut-off range for the membrane is from about 30,000 to about 150,000 daltons, preferably about 50,000 to about 100,000 daltons. For continuous operation, the membranes are dimensioned to permit the desired degree of concentration as the aqueous protein solution passes through the membranes.

The first ultrafiltration step may be effected to concentrate the aqueous protein solution from about 4 to about 20 fold to a protein concentration of at least about 50 g/L, preferably at least about 200 g/L and more preferably at least about 250 g/L.

The concentrated protein solution preferably then is subjected to a diafiltration step using an aqueous salt solution of the same molarity and pH as the extraction solution. An antioxidant may be present in the diafiltration medium during at least part of the diafiltration step to inhibit oxidation of phenolics in the concentrated canola protein isolate solution. The antioxidant may be any convenient antioxidant, such as sodium sulfite or ascorbic acid. The quantity of antioxidant employed in the diafiltration medium depends on the material employed and may vary from about 0.01 to about 1 wt %, preferably about 0.05 wt %.

The diafiltration step may be effected by using from about 2 to about 20 volumes of diafiltration solution, preferably about 5 to about 10 volume of diafiltration solution. During the diafiltration operation, 2S protein phenolics and visible colour components along with other low molecular weight components are removed from the concentrated protein solution by passage through the membrane with the permeate.

The diafiltration step may be effected using the same membrane as used for the concentration step.

The concentration step and the diafiltration step may be effected at any convenient temperature, generally about 20° to about 60° C., preferably below about 30° C., and for a period of time to effect the desired degree of concentration and washing. The temperatures and other conditions used depend to some degree on the membrane equipment used to effect the concentration and the desired protein concentration of the solution.

The membrane used in the first ultrafiltration step permits a significant proportion of the 2S protein to pass into the permeate, along with other low molecular weight species, including the ionic species of the food grade salt, carbohydrates, phenolics, pigments and anti-nutritional factors. The molecular weight cut-off is normally chosen to ensure retention of a significant proportion of the 7S and 12S protein in the retentate, while permitting the 2S protein and contaminants to pass through, having regard to the different membrane materials and configurations.

The retentate from the concentration step and optional diafiltration step then is dried by any convenient technique, such as spray drying or freeze drying, to a dry form. The dried protein has a high protein content, in excess of about 90 wt % protein, preferably at least about 100 wt % protein (N×6.25), and is substantially undenatured (as determined by differential scanning calorimetry). The dried protein isolate consists predominantly of the canola 7S protein, with some 12S protein and possibly small quantities of 2S protein. In general, the dried canola protein isolate contains:

about 60 to about 95 wt % of 7S protein
about 2 to about 15 wt % of the 12S protein
0 to about 30 wt % of the 2S protein
Preferably, the dried canola protein isolate contains:
about 70 to about 90 wt % of 7S protein
about 5 to about 10 wt % of the 12S protein
0 to about 20 wt % of the 2S protein The permeate from the concentration step and optional diafiltration step is concentrated in a second ultrafiltration step using membranes, such as hollow-fibre membranes or spiral wound membranes, having a suitable molecular weight cut-off to retain the 2S protein while permitting low molecular weight species, including salt, phenolics, colour components and anti-nutritional factors, to pass through the membrane. Ultrafiltration membranes having a molecular weight cut-off of about 3,000 to about 30,000 daltons, preferably about 5,000 to about 10,000 daltons, having regard to differing membrane materials and configurations, may be used. The permeate generally is concentrated to a protein concentration of at least about 50 g/L, preferably about 100 to about 400 g/L, more preferably about 200 to about 300 g/L, prior to drying. Such a concentration operation may be carried out in a batch mode or in a continuous operation, as described above for the protein solution concentration step.

The concentrated permeate may be subjected to a diafiltration step using water. An antioxidant may be present in the diafiltration medium during at least part of the diafiltration step to inhibit oxidation of phenolics in the concentrated permeate. The antioxidant may be any convenient antioxidant, such as sodium sulfite or ascorbic acid. The quantity of antioxidant employed in the diafiltration medium depends on the material employed and may vary from about 0.01 to about 1 wt %, preferably about 0.05 wt %.

The diafiltration step may be effected using 2 to 20 volumes of diafiltration solution, preferably about 5 to about 10 volumes of diafiltration solution. In the diafiltration operation, further quantities of contaminants, including phenolics and visible colour components, are removed from the concentrated permeate by passage through the diafiltration membrane. The diafiltration operation may be effected until no significant further quantities of phenolics and visible colour components are removed in the permeate.

The diafiltration step may be effected using the same membrane as used in the concentration step. Alternatively, a separate membrane may be used having a molecular weight cut-off in the range of about 3000 to about 50,000 daltons, preferably about 5,000 to about 10,000 daltons, having regard to different membrane materials and configurations.

The concentrated and optionally diafiltered permeate is dried by any convenient technique, such as spray drying or freeze drying, to a dry form. The dried protein has a high protein content, in excess of about 90 wt % protein, preferably at least about 100 wt % (N×6.25), and is substantially undenatured (as determined by differential scanning calorimetry).

The dried canola protein isolate consists predominantly of the canola 2S protein with small quantities of 7S protein. In general, the dried canola protein isolate contains:

about 85 to about 100 wt % of 2S protein
0 to about 15 wt % of 7S protein,
preferably about 90 to about 100 wt % of 2S protein
0 to about 10 wt % of 7S protein If desired, a portion of the concentrated canola protein isolate from the first ultrafiltration step may be combined with a portion of the concentrated permeate from the second ultrafiltration step prior to drying the combined streams by any convenient technique to provide a combined canola protein isolate composition. The relative proportions of the proteinaceous materials mixed together may be chosen to provide a resulting canola protein isolate composition having a desired profile of 2S/7S/12S proteins. Alternatively, the dried protein isolates may be combined in any desired proportion to provide any desired specific 2S/7S/12S protein profile in the mixtures. The combined canola protein isolate composition has a high protein content, in excess of about 90 wt %, preferably at least about 100 wt % (calculated as N×6.25), and is substantially undenatured (as determined by differential scanning calorimetry).

By operating in this manner, a number of canola protein isolates may be recovered as dry mixtures of various proportions by weight of first ultrafiltration-derived canola protein isolate and second ultrafiltration-derived canola protein isolate, generally about 5:95 to about 95:5 by weight, which may be desirable for attaining differing functional and nutritional properties based on the differing proportions of 2S/7S/12S proteins in the compositions.

DESCRIPTION OF PREFERRED EMBODIMENT

Referring to FIG. 1, there is shown therein the two-membrane process provided in accordance with one aspect of the invention in comparison to the formation of canola protein isolates (CPIs) by the micelle mute.

As can be seen, retentate from a first ultrafiltration stage (Ultrafiltration #1), which may comprise ultrafiltration and diafiltration steps, is processed in one of two ways. In the two-membrane process of the invention, the retentate is spray dried to provide a canola protein isolate which consists predominantly of 7S canola protein.

In the procedure of the aforementioned U.S. patent application Ser. No. 10/137,321, the retentate is passed to a dilution step in which canola protein isolate is precipitated as a protein micellar mass. The protein micellar mass is spray dried to provide a canola protein isolate consisting predominantly of 7S canola protein.

In the two-membrane process of the invention, the permeate from the first ultrafiltration step is subjected to a second ultrafiltration step (Ultrafiltration #2-A), which may include ultrafiltration and diafiltration. The retentate from the second ultrafiltration step is spray dried to provide a canola protein isolate consisting predominantly of 2S protein.

In the procedure of U.S. Ser. No. 10/137,321, the supernatant from the precipitation of the protein micellar mass is subjected to an ultrafiltration step Ultrafiltration #2-B), which may include ultrafiltration and diafiltration. The retentate from the ultrafiltration step is spray dried to provide a canola protein isolate consisting predominantly of the 2S protein.

As described above, the retentate from the latter ultrafiltration step may be heat-treated to reduce the proportion of 7S protein in the retentate and to provide the canola protein isolate of the invention.

This Example describes the production of a canola protein isolate in accordance with one embodiment of the invention.

EXAMPLES

Example 1

This Example describes the production of a novel canola protein isolate in accordance with one embodiment of the invention.

'a' kg of canola meal was added to 'b' L of 0.1 M NaCl solution at ambient temperature and agitated for 30 minutes to provide an aqueous protein solution. The residual canola meal was removed and the resulting protein solution was clarified by centrifugation and filtration to produce 'c' L of filtered protein solution having a protein content of 'd' % by weight.

A 'e' L aliquot of the protein extract solution was reduced in volume to 'f' L by concentration on a polyvinylidene difluoride (PVDF) membrane having a molecular weight cut-off of 5,000 daltons and then diafiltered with 'g' L of 0.1M NaCl solution on the same membrane. The diafiltered retentate was then pasteurized at 60° C. for 10 minutes. The resulting pasteurized concentrated protein solution had a protein content of 'h' % by weight.

The concentrated solution at 'i'° C. was diluted 'j' into cold RO water having a temperature 'k'° C. A white cloud formed immediately and was allowed to settle. The upper diluting water was removed and the precipitated, viscous, sticky mass (PMM) was recovered from the bottom of the vessel in a yield of 'l' wt % of the filtered protein solution. The dried PMM derived protein was found to have a protein content of 'm' % (N×6.25) d.b. The product was given a designation 'n' C300.

The parameters 'a' to 'n' for two runs are set forth in the following Table

TABLE I

| n | BW-SA034-J12-04A | BW-SA035-J14-04A |
|---|---|---|
| a | 15 | 15 |
| b | 150 | 150 |
| c | 75 | 68 |
| d | 1.93 | 1.95 |
| e | 75 | 68 |
| f | 4 | 4 |
| g | 20 | 20 |
| h | 19.08 | 14.20 |
| i | 33 | 33 |
| j | 1:10 | 1:10 |
| k | 3 | 3 |
| l | 37.45 | 28.32 |
| m | 103.08 | 99.73 |

The removed supernatant was reduced in volume to 'o' L by ultrafiltration using a polyethersulfone (PES) membrane having a molecular weight cut-off of 10,000 daltons and then the concentrate was diafiltered on the same membrane with 'p' L of water. The diafiltered concentrate was then pasteurized at 60° C. for 10 minutes. The pasteurized concentrate contained 'q' % protein by weight. With the additional protein recovered from the supernatant, the overall protein recovery of the filtered protein solution was 'r' wt %. The pasteurized concentrate was split into two equal portions. One portion was spray dried to form a final product given designation 'n' C200 and had a protein content of 's'% (N×6.25) d.b.

The parameters 'n' to 's' for two runs are set forth in the following Table II:

TABLE II

| n | BW-SA034-J12-04A | BW-SA035-J14-04A |
|---|---|---|
| o | 3.5 | 3 |
| p | 7 | 6 |
| q | 4.83 | 4.30 |
| r | 49.35 | 38.05 |
| s | 91.73 | 93.69 |

The other portion of the pasteurized, concentrated supernatant was heated to 85° C. for 10 minutes and then centrifuged to remove precipitated protein. The resulting concentrate was then spray dried to form a final product given designation 'n' C200H and had a protein content of 't' % (N×6.25). The parameters 'n' and 't' for two runs are set forth in the following Table III:

TABLE III

| n | BW-SA034-J12-04A | BW-SA035-J14-04A |
|---|---|---|
| t | 91.32 | 92.11 |

Example 2

This Example shows the effect of heating temperature and time on the protein profile of canola protein isolate produced from concentrated supernatant.

A solution of C200 canola protein isolate from batch SA035-J14-04A, prepared as described in Example 1, was prepared in reverse osmosis purified water to a protein concentration of 5 wt %. The solution was prepared by stirring the protein and water with a magnetic stir bar for one hour at room temperature.

Samples of the protein solution (25 ml) were heated in centrifuge tubes in a temperature controlled water bath. Samples were heated for 10 minutes at a temperature of 75, 80, 85, 90 or 95° C. Timing started when the internal temperature of the sample was within 1° C. of the desired level and the samples were mixed constantly throughout the heating process. After heat treatment, the samples were centrifuged at 8,000 g for 10 minutes and the supernatants analyzed for protein profile by size exclusion HPLC.

The results obtained are set forth in the following Table IV:

TABLE IV

Protein profiles of C200 solutions heated to different temperatures

| Treatment temperature | %7S | %2S |
|---|---|---|
| Control (no heat) | 22.6 | 77.4 |
| 75° C. | 5.3 | 94.7 |
| 80° C. | 3.6 | 96.4 |
| 85° C. | 3.5 | 96.5 |
| 90° C. | 1.8 | 98.2 |
| 95° C. | 1.8 | 98.2 |

As may be seen from the results set forth in Table IV, all the heat treatments applied resulted in a significant reduction in 7S protein from the samples. Treatment at 90° C. resulted in the lowest level of 7S and no additional improvement was gained by raising the temperature to 95° C. It was determined by size exclusion HPLC analysis that the heat treatment had little effect on the peak area for 2S. This means that the heat treatment resulted in minimal loss of 2S protein.

A sample of protein solution (80 ml) was heated in a jacketed vessel attached to a circulating water bath set to a temperature of 90° C. and the sample was mixed with a magnetic stir bar. Aliquots of heated solution were removed after 5, 10 and 15 minutes of heating time. Timing did not start until the temperature of the sample measured 85° C. After heat treatment, the collected samples were centrifuged at 8,000 g for 10 minutes and the supernatants submitted for analysis.

The results obtained are set forth in the following Table V:

TABLE V

Protein profiles of C200 solutions heated for different lengths of time

| Treatment time | %7S | %2S |
|---|---|---|
| Control (no heat) | 22.6 | 77.4 |
| 5 min | 1.8 | 98.2 |
| 10 min | 1.9 | 98.1 |
| 15 min | 1.9 | 98.1 |

As may be seen from the results set forth in Table V, there was no significant difference in the level of 7S protein in the samples for any of the tested times.

As is apparent from the results outlined in this Example, a significant reduction in the level of 7S protein in concentrated supernatant can be obtained with a wide variety of heating conditions.

Example 3

This Example contains an evaluation of protein profiles for the canola protein isolates produced according to Example 1.

Size exclusion HPLC was used to evaluate the protein profile of the concentrated supernatant and modified concentrated supernatant produced according to the procedures of Example 1. The spray dried products were dissolved at a 1 wt % level in 0.1 M NaCl prior to HPLC analysis.

The results obtained are set forth in the following Table VI:

TABLE VI

| Batch | Product | %12S | %7S | %2S |
|---|---|---|---|---|
| SA034-J12-04A | Concentrated supernatant (C200) | 0.00 | 13.13 | 86.67 |
|  | Modified concentrated supernatant (C200H) | 0.00 | 3.55 | 96.45 |
| SA035-J14-04A | Concentrated supernatant (C200) | 0.00 | 24.52 | 75.48 |
|  | Modified concentrated supernatant (C200H) | 000 | 7.55 | 92.45 |

As may be seen from the results set forth in Table VI, the heat treatment of the concentrated supernatant results in a significant reduction of the quantity of 7S protein in the spray dried canola protein isolate compared to the absence of such heat treatment.

Example 4

This Example contains an evaluation of the solubility of the canola protein isolates produced in Example 1.

The solubility of the spray dried concentrated supernatant (C200) and modified concentrated supernatant (C200H) produced by the procedures of Example 1, was determined using a modified version of the procedure of Morr et al, J. Food Sci. 50:1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (4, 5, 6 or 7) with NaOH or HCl. A sample was also prepared at native pH. For the pH adjusted samples, the pH was measured and corrected two times during the 60 minutes stirring. After the 60 minutes of stirring, the sample was made up to 50 ml total volume with RO water, yielding a 1% w/v protein dispersion. An aliquot of the protein dispersion was reserved for protein content determination by Leco analysis using a Leco FA28 Nitrogen Determinator. Another portion of the sample was centrifuged at 8000 g for 10 minutes. This sedimented any undissolved material and yielded a clear supernatant. The protein content of the supernatant was then determined by Leco analysis.

Solubility(%)=(Supernatant protein conc./Original dispersion protein conc.)×100

The results obtained are set forth in the following Table VII:

TABLE VII

| Batch | Product | Solubility (%) | | | | |
|---|---|---|---|---|---|---|
| | | pH 4 | pH 5 | pH 6 | pH 7 | Native pH |
| SA034-J12-04A | Concentrated supernatant | 88.1 | 100 | 86.1 | 97.3 | 89.8 |
| | Modified concentrated supernatant | 100 | 100 | 100 | 100 | 100 |
| SA035-J14-04A | Concentrated supernatant | 87.4 | 95 | 90.6 | 90.6 | 86.7 |
| | Modified concentrated supernatant | 100 | 100 | 100 | 100 | 100 |

As can be seen from the results of Table VII, the dried isolate from modified concentrated supernatant (C200H) was notably more soluble in water at various pH values than the dried isolate from concentrated supernatant (C200).

Example 5

This Example contains an evaluation of the solubility of the canola protein isolates produced in Example 1 in a soft drink.

The solubility in a soft drink of the spray dried concentrated supernatant and modified concentrated supernatant, produced by the procedures of Example 1, were determined using a modification of the procedure of Morr et al, J. Food Sci. 50:1715-1718.

Sufficient protein powder to supply 1.0 g of protein was weighed into a beaker and then a small amount of a colourless, transparent, commercial carbonated soft drink was added and the mixture stirred until a smooth paste formed. Additional soft drink was then added to bring the volume to approximately 45 ml. The contents of the beaker were then slowly stirred for 60 minutes using a magnetic stirrer. After the 60 minutes of stirring, the sample was made up to 50 ml total volume with soft drink, yielding a 2% w/v protein dispersion. An aliquot of the protein dispersion was reserved for protein content determination by Leco analysis. Another portion of the sample was centrifuged at 8,000 g for 10 min. This sedimented any undissolved material and yielded a clear supernatant. The protein content of the supernatant was then determined by Leco analysis.

Solubility(%)=(supernatant protein conc./Original dispersion protein conc.)×100

The results obtained are set forth in the following Table VIII:

TABLE VIII

| Batch | Product | Solubility (%) |
|---|---|---|
| SA034-J12-04A | Concentrated supernatant | 92.3 |
| | Modified concentrated supernatant | 94.9 |
| SA035-J14-04A | Concentrated supernatant | 96.1 |
| | Modified concentrated supernatant | 94.4 |

As may be seen from the results of Table VIII, the dried isolate from modified concentrated supernatant (C200H) and concentrated supernatant (C200) had similar solubilities in the soft drink.

However, as may be seen from the results of Example 6 below, the clarity of the solution prepared from the dried isolate from modified concentrated supernatant was far superior.

Example 6

This Example contains an evaluation of the clarity in solutions of spray dried isolates produced in Example 1 dissolved in a soft drink.

The clarity in a soft drink of solutions of spray dried isolates from modified concentrated supernatant and concentrated supernatant, produced as described in Example 1, was determined. Clarity was assessed by measuring the absorbance of visible light at 600 nm by a solution of 2% w/v protein in a colourless, transparent, commercial carbonated soft drink. The lower the absorbance reading, the better light was being transmitted and the better the clarity of the solution.

The results obtained are set forth in the following Table IX:

TABLE IX

| Batch | Product | A600 |
|---|---|---|
| SA034-J12-04A | Concentrated supernatant | 0.544 |
| | Modified concentrated supernatant | 0.150 |
| SA035-J14-04A | Concentrated supernatant | 1.920 |
| | Modified concentrated supernatant | 0.367 |

As may be seen from the results of Table IX, the clarity of the solution prepared from the spray dried isolate from modified concentrated supernatant (C200H) was far superior to that prepared from the spray dried concentrated supernatant (C200).

Example 7

This Example illustrates an alternative process of forming the canola protein isolate of the invention (FIG. 1).

15 kg of canola oil seed meal was added to 100 L (15% w/v) of 0.15M sodium chloride solution containing 0.05 wt % ascorbic acid at ambient temperature in a 350 L extraction tank and the mixture was agitated for 30 minutes to provide a canola protein solution having a concentration of 20 g/L. Bulk residual meal was removed by using a basket centrifuge with a 400 mesh bag and the separated bulk meal was discharged to waste. The canola protein solution was given a second pass through the basket centrifuge using a 600 mesh bag to remove suspended fine particles. The resulting canola protein solution was polished using a filter press with 2 μm filter pads.

The clarified canola protein solution was subjected to an ultrafiltration step using a spiral wound polyvinylidiene difluoride (PVDF) membrane with a molecular weight cut-off of 100,000 daltons at ambient temperature to concentrate the canola protein solution containing 7S and 12S proteins to a volume of 4.3 L and a protein concentration of 188 g/L. The permeate from the ultrafiltration step contained the 2S protein along with other low molecular weight species.

The concentrated canola protein solution (retentate) then was subjected to a diafiltration step using the same membrane as for the ultrafiltration using an aqueous 0.15 M sodium chloride solution containing 0.05 wt % ascorbic acid. The diafiltration medium was added to the retentate at the same flow rate as permeate was removed from the membrane. The diafiltration was carried out with 5 retentate volumes of diafiltration medium.

A 1.25 L aliquot of the retentate from the ultrafiltration and diafiltration operations was spray dried to provide a canola protein isolate consisting predominantly of 7S protein, having a protein content of 99.1 wt % (N×6.25, percent nitrogen values were determined using a Leco FP528 Nitrogen Determinator) d.b. and containing 18.21 wt % 2S protein, 74.55 wt % 7S protein and 7.24 wt % 12S protein.

The permeate from the ultrafiltration and diafiltration operations was subjected to an ultrafiltration step using a spiral wound polyethersulfone (PES) membrane with a molecular weight cut-off of 5000 daltons to permit retention of 2S protein and to permit low molecular weight contaminants to pass through the membrane to waste. This ultrafiltration step was effected at ambient temperature to concentrate the 2S-containing permeate from the first ultrafiltration step to 3 L having a protein concentration of 125 g/L.

The concentrated canola 2S protein solution (retentate) then was subjected to a diafiltration step using the same membrane as for the ultrafiltration using filtered tap water as the diafiltration medium. The water was added to the retentate at the same flow rate as permeate was removed from the membrane. The diafiltration was carried out with 5 retentate volumes of diafiltration medium.

The retentate from the diafiltration step was spray dried to provide a canola protein isolate consisting predominantly of 2S protein, having a protein content of 105.8 wt % (N×6.25) d.b. and containing 96.7 wt % 2S protein, 3.3 wt % 7S protein and 0.04 wt % 12S protein.

Example 8

This Example is a repeat of the process of Example 7, but on a larger scale.

150 kg of canola oil seed meal was added to 1000 L (15% w/v) of 0.15 M sodium chloride solution containing 0.05 wt % of ascorbic acid at ambient temperature in a 10,000 L extraction tank and the mixture was agitated for 30 minutes to provide a canola protein solution having a concentration of 20.7 g/L. Bulk residual meal was removed by using a vacuum filter belt and the separated meal was discharged to waste. The canola protein solution was clarified by using a disc centrifuge and the desludged solids discharged to waste. The resulting canola protein solution was polished using a filter press with 2 μm filter pads followed by another one with 0.2 μm pads.

The clarified canola protein solution was subjected to ultrafiltration using two spiral wound PVDF membranes with a molecular weight cut-off of 100,000 daltons to concentrate the canola protein solution containing 7S and 12S proteins to 41.1 L having a protein concentration of 221 g/L. The permeate from the ultrafiltration step contained the 2S protein along with other low molecular weight species.

A 3 L aliquot of the retentate from the ultrafiltration operation was spray dried to provide a canola protein isolate consisting predominantly of 7S protein, having a protein content of 95.1 wt % (N×6.25) d.b. and containing 26.86 wt % of 2S protein, 66.22 wt % of 7S protein and 6.92 wt % of 12S protein.

The permeate from the ultrafiltration operation was subjected to an ultrafiltration step using two spiral wound PVDF membranes with a molecular weight cut-off of 5,000 daltons to permit retention of 2S protein and to permit low molecular weight contaminants to pass through the membrane to waste. This ultrafiltration step was effected at ambient temperature to concentrate the 2S-containing permeate from the first ultrafiltration step to 25 L having a protein concentration of 24.2 g/L.

The retentate from the ultrafiltration step was spray dried to form a non-diafiltered canola protein product having a protein concentration of 47.94 wt % (N×6.25) d.b. and containing 94.64 wt % of 2S protein, 5.36 wt % of 7S protein and 0 wt % of 12S protein.

The low protein content of the latter canola protein product was due to the absence of a diafiltration step to remove the salt and other impurities. Later bench diafiltration with this product given results that indicated the production of a canola protein isolate after diafiltration.

Example 9

This Example provides a comparison of the canola protein isolate products prepared according to the procedure of Example 8 with canola protein isolate products prepared by the micelle route.

A 34 L aliquot of the retentate from the first ultrafiltration step described in Example 7 was warmed to 29.8° C. and poured into chilled water having a temperature of 3.7° C. at a ratio of 10 volumes of water per volume of retentate. A white cloud of protein micelles immediately formed. The micelles were allowed to coalesce and settle overnight. The accumulated protein micellar mass was separated from supernatant and was spray dried to provide a canola protein isolate having a protein content of 107.4 wt % (N×6.25) d.b. and containing 3.80 wt % 2S protein, 85.88 wt % 7S protein and 10.32 wt % 12S protein.

The supernatant from the PMM-settling step (365 L) was subjected to an ultrafiltration step using a spiral wound PVDF membrane with a molecular weight cut-off of 5000 daltons to permit retention of 2S protein and 7S protein and to permit low molecular weight contaminants to pass through the membrane to waste. This ultrafiltration step was effected at ambient temperature to concentrate the supernatant to 22 L having a protein content of 89.3 g/L.

The concentrated supernatant was spray dried to provide a canola protein isolate consisting predominantly of 2S protein, having a protein content of 95.51 wt % (N×6.25) d.b. and containing 84.01 wt % 2S protein, 15.51 wt % 7S protein and 0.48 wt % of 12S protein.

SUMMARY OF DISCLOSURE

In summary of this disclosure, a canola protein isolate having an increased content of 2S protein and a reduced quantity of 7S protein is provided having utility in producing clear aqueous solutions, particularly in soft drinks. Modifications are possible within the scope of the invention.

What we claim is:

1. A process for the preparation of a canola protein isolate having an increased proportion of 2S canola protein, which comprises:
   (a) providing an aqueous solution of 2S and 7S canola proteins consisting predominantly of 2S canola protein, said aqueous solution being in the form of concentrated supernatant from canola protein micelle formation and precipitation, wherein said canola protein micelle formation is effected by:
      (i) extracting canola oil seed meal at a temperature of at least 5° C. to cause solubilization of protein in said canola oil seed meal and to form an aqueous protein solution,
      (ii) separating said aqueous protein solution from residual oil seed meal,
      (iii) increasing the concentration of said aqueous protein solution to at least 200 g/L while maintaining the ionic strength substantially constant by a selective membrane technique to provide a concentrated protein solution,
      (iv) diluting said concentrated protein solution into chilled water having a temperature of below 15° C. to cause the formation of the protein micelles, and
      (v) separating supernatant from settled protein micellar mass,
   (b) heat treating said supernatant by heating the supernatant for about 5 to about 15 minutes at a temperature of about 75° to about 95° C. to cause precipitation of 7S canals protein,
   (c) removing precipitated 7S protein from the heat-treated supernatant, and
   (d) recovering from the supernatant resulting from step (c), which supernatant is a canola protein isolate having a protein content of at least 90 wt % (N×6.25) on a dry weight basis and having an increased proportion of 2S canola protein as compared to the aqueous solution of 2S and 7S canola proteins.

2. The process of claim 1 wherein said supernatant is concentrated to a protein concentration of about 100 to about 400 g/L prior to said heat treatment.

3. The process of claim 2 wherein said supernatant is concentrated to a protein concentration of about 200 to about 300 g/L.

4. The process of claim 2 wherein said concentration step is effected by ultrafiltration using a membrane having a molecular weight cut-off about 3,000 to about 100,000 daltons.

5. The process of claim 4 wherein the concentrated supernatant resulting from ultrafiltration is subjected to diafiltration prior to said heat treatment step.

6. The process of claim 5 wherein said diafiltration step is effected using from about 2 to about 20 volumes, preferably about 5 to about 10 volumes, of water using a membrane having a molecular weight cut-off of about 3,000 to about 100,000 daltons.

7. The process of claim 1 wherein said canola protein isolate has a protein content of at least 100 wt % (N×6.25) dry basis.

* * * * *